United States Patent [19]

LeVeen et al.

[11] Patent Number: 4,520,823

[45] Date of Patent: Jun. 4, 1985

[54] CATHETER WITH SEPARABLE BALLOONS

[76] Inventors: Harry H. LeVeen, 321 Confederate Cir., Charleston, S.C. 29407; Robert F. LeVeen, 312 Lombard St., Philadelphia, Pa. 19147; Eric G. LeVeen, 358 Summit Ave., Mount Vernon, N.Y. 10552

[21] Appl. No.: 533,755

[22] Filed: Sep. 19, 1983

Related U.S. Application Data

[63] Continuation-in-part of Ser. No. 250,603, Apr. 3, 1981, Pat. No. 4,404,971.

[51] Int. Cl.³ .......................................... A61M 25/00
[52] U.S. Cl. ................................ 128/348.1; 128/325; 604/101
[58] Field of Search ................... 128/325, 344, 348.1, 128/334; 604/101

[56] References Cited

U.S. PATENT DOCUMENTS

| 3,833,003 | 9/1974 | Taricco | 128/325 X |
| 3,991,767 | 11/1976 | Miller et al. | 128/334 R X |
| 4,130,119 | 12/1978 | Sessions et al. | 128/325 |
| 4,140,126 | 2/1979 | Choudhury | 128/325 |
| 4,404,971 | 9/1983 | LeVeen et al. | 128/325 X |
| 4,456,011 | 6/1984 | Warnecke | 128/325 |

Primary Examiner—Dalton L. Truluck
Attorney, Agent, or Firm—Brooks Haidt Haffner & Delahunty

[57] ABSTRACT

A catheter having first and second inflatable balloon structures with a valved coupling permitting the balloon structures to be separated while remaining inflated.

4 Claims, 9 Drawing Figures

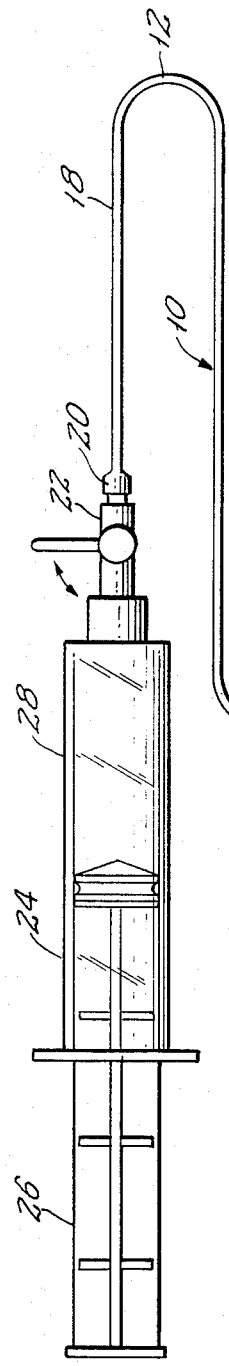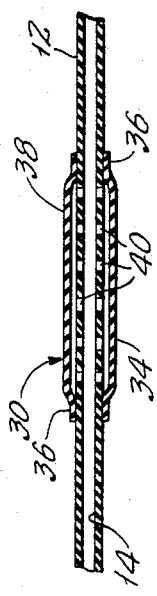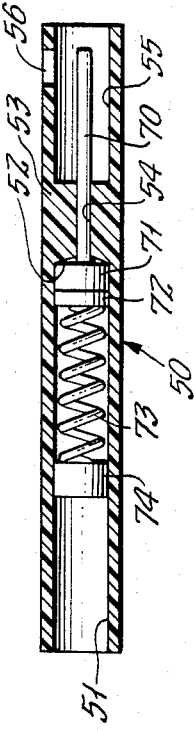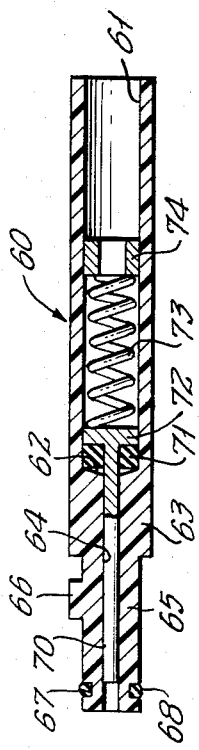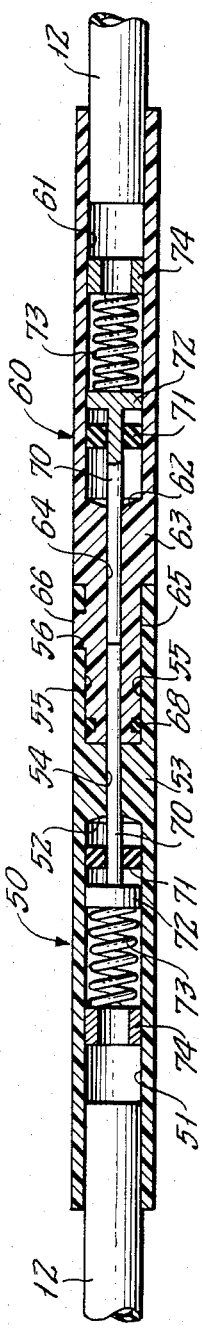

CATHETER WITH SEPARABLE BALLOONS

This application is a continuation-in-part of copending application Ser. No. 250,603 filed Apr. 3 1981, now U.S. Pat. No. 4,404,971 issued Sept. 20, 1983.

This invention relates to vascular surgery and in particular provides a balloon catheter having particular utility in obturating blood flow in the treatment of aneurysms and the like.

The dual balloon catheter has been found useful in surgery not only for rapidly closing bleeding wounds by obturating blood flow on both sides of a wound in a blood vessel, but also in the treatment of aneurysms. In the treatment of aneurysms, however, it is frequently desirable to introduce a prothesis in the form of tubing to replace a section of blood vessel containing the aneurysm. As the positioning of such a prothesis requires resection of the blood vessel in order for the tubing to replace the section of blood vessel containing the aneurysm, it is necessary to cut off the flow of blood separately in the portions of the blood vessel which are severed during the resection.

It is thus a principal object of this invention to provide a dual balloon catheter for obturating flow in a blood vessel or the like at two spaced points in which the balloons can be separated while inflated and obturating blood flow.

It is also an important object of this invention to provide a valved coupling within a catheter permitting the catheter to be separated without loss of internal pressure.

These and other objects of the invention are essentially obtained utilizing a catheter having a pair of inflatable balloons located adjacent an end of the catheter, such as described in our above noted copending application Ser. No. 250,603. In accordance with that invention the balloons are inflated by introduction of a fluid, such as air under pressure, into the interior of the catheter through a remote end of the catheter which is connected to a suitable device for so introducing such a fluid, for example, a syringe. The catheter should further be provided at its end connected to the fluid pressuring device with some means of retaining fluid pressure in the catheter.

In accordance with this invention the section of catheter joining the two balloons is provided with a valved coupling including a pair of conduits, one connected to each balloon, which are arranged to fit together and provide fluid-tight communication between the two balloons within the catheter section. Each of the conduits in accordance with this invention is provided with a spring-loaded, normally closed valve. Each valve is provided with an actuating member including a reciprocable pin which is disposed lengthwise in the conduit. The pins are sized and positioned to engage each other upon mating of the two conduits in such a manner that the valves are opened against their spring biasing by the mating action to establish communication between the two conduits and hence the interior of the catheter section.

For a more complete understanding of the practical application of this invention reference is made to the appended drawings in which:

FIG. 1 is an elevational view of a catheter in accordance with the present invention including a pair of spaced inflatable balloons which can be separated under pressure;

FIG. 2 is a fragmentary section of the catheter showing the balloon construction;

FIG. 3 is a longitudinal section through a valved coupling part;

FIG. 4 is a longitudinal section through a second valved coupling part designed to mate with the coupling part shown in FIG. 3;

FIG. 5 is a view similar to FIGS. 3 and 4 showing the two coupling parts in mating position.

Figure 7:
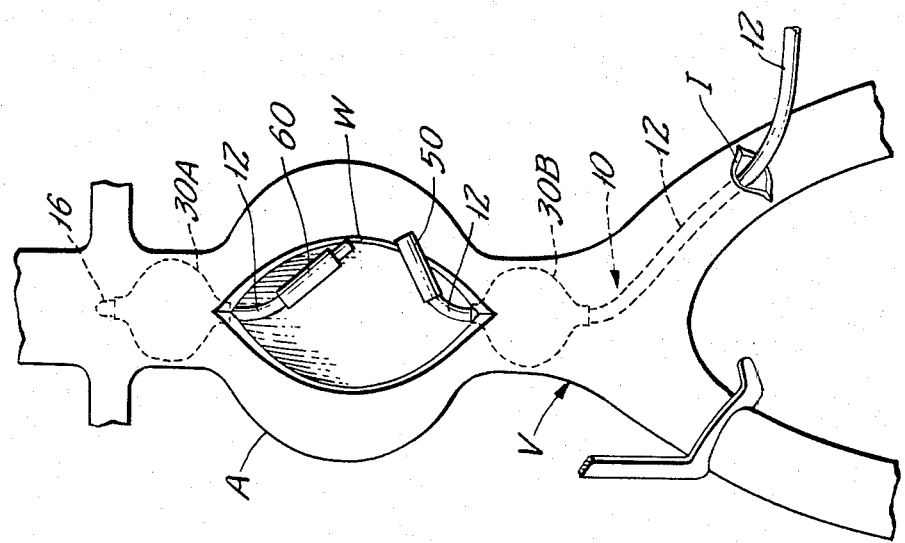
FIGS. 6 through 9 are a series of views showing in sequence the employment of the valved catheter of this invention in the treatment of an aneurysm for removal of the section of blood vessel containing the aneurysm and its replacement with a prothesis.
Figure 6:
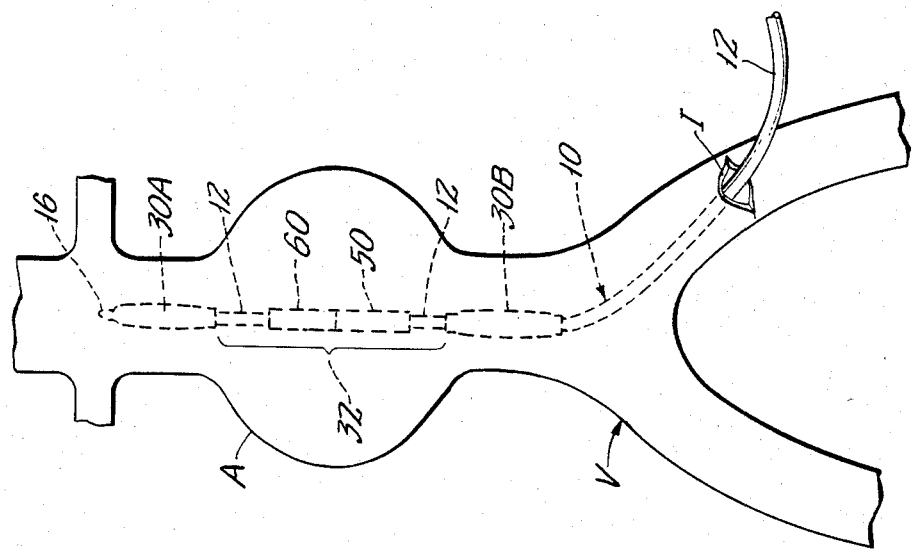

Referring more particularly to FIG. 1 the reference numeral 10 generally indicates a dual balloon catheter similar to that described in our copending application Ser. No. 250,603. Catheter 10 includes an elongated tube 12 constructed of polyurethane or similar inert material having central bore 14 (see FIG. 2) extending throughout its length. At one end 16 of catheter 10 bore 14 of tube 12 is closed. At the other end 18 a male luer fitting 20 is provided which communicates interiorally with bore 14 and which is received in corresponding female fitting of a one-way valve 22 mounted on a syringe 24. Valve 22 has a position closing off communication to bore 14 and a second position communicating bore 14 with the interior of syringe 24 such that by forcing the plunger 26 of syringe 24 into its barrel 28 fluid (normally air) contained with barrel 28 is forced into bore 14.

Catheter 10 is provided with two balloon forming structures 30, one of which is shown in section in FIG. 2. For convenience, in the other figures, one balloon forming structure is designated as 30A and is located adjacent closed end 16 of catheter 10. The other balloon forming structure is designated in those other figures as 30B and is located away from end 16 spaced apart from balloon forming structure 30A by a short catheter section indicated by the reference numeral 32 in FIG. 1.

Referring more particularly to FIG. 2, each balloon forming structure 30 includes a more or less cylindrical wall in the form of a sleeve 34 snugly overlying and extended about tube 12. Sleeve 34 is formed of rubber or other inert elastomeric material and is sufficiently thin that it is freely extendible with little force. Sleeve 34 is secured to tube 12 at its ends, with a fluid tight seal formed by wrapping the ends with a serving of silk thread indicated by the reference numeral 36. Thus an annular space 38 is trapped between the exterior of tube 12 and the interior of sleeve 34. A series of ports 40 through tube 12 communicate the interior of bore 14 with annular space 38.

Catheter section 32, referring more particularly to FIGS. 3, 4 and 5, includes a female coupling 50 and a male coupling 60 which join, as shown in FIG. 5, tubing 12 passing through balloon 30B and tubing 12 passing through balloon 30A.

Coupling member 50, as shown more fully in FIG. 3, is formed of a cylindrical length of hard, inert plastic material which at one end (left in FIG. 3) has an open axial bore 51 extending past the middle of part 50 and terminating in a conical seat 52. A thicker intermediate portion 53 in member 50 has a small axial bore 54 leading from seat 52 toward the end of coupling part 50 remote from bore 51. Member 50 is also provided with a large bore 55 opening in the end remote from bore 51 which leads to the thickened intermediate portion 53 of coupling part 50 such that small bore 54 provides fluid communication between bore 51 and bore 55. An opening 56 from bore 55 through the wall of member 50 is formed adjacent the right end of member 50, as seen in FIG. 3.

An annular silicone rubber gasket 71 is positioned on conical seat 52, and an elongated stainless steel pin 70 having an integral flat head 72 is positioned with pin 70 extending axially in portion 53 through narrow bore 54 and annular rubber gasket 71 such that head 72 is in bore 51 and bears against the side of gasket 71 opposite seat 52. The end of pin 70 remote from head 72 terminates in bore 55. A stainless steel coil spring 73 is positioned in bore 51 retained under slight compression against head 72 by a stainless steel ring 74 wedged in bore 51 such that the compression exerted by spring 73 against head 72 is sufficient to seal gasket 71 between head 72 and seat 52 and block fluid flow about pin 70 through bore 54.

Coupling member 60, as shown more fully in FIG. 4, is formed of a cylindrical length of hard, inert plastic material which at one end (right in FIG. 4) has an open axial bore 61 extending past the middle of part 60 and terminating in a conical seat 62. A thicker intermediate portion 63 in member 60 has a small axial bore 64 leading from seat 62 to the end of coupling part 60 remote from bore 61. Member 60 at its end remote from bore 61 has a reduced diameter to form a plug portion 65 sized to fit into bore 55 of member 50. Small bore 64 thus provides fluid communication from bore 61 through portion 63 and plug 65 to the end of member 60 remote from bore 61. A stud 66 is formed on plug 65 adjacent the right end of pins 65, as seen in FIG. 4. Adjacent its left end plug 65 is provided with a small circumferential groove 67 which receives a silicone rubber O-ring 68.

An annular silicone rubber gasket 71 is positioned on conical seat 62 and an elongated stainless steel pin 70 having an integral flat head 72 is positioned with pin 70 extending axially into narrow bore 64 and annular rubber gasket 71 such that head 72 bears against the side of gasket 71 opposite seat 62. A stainless steel coil spring 73 is positioned in bore 61 retained under slight compression against head 72 by a stainless steel ring 74 wedged in bore 61 such that the compression exerted by spring 73 against head 72 is sufficient to seal gasket 71 between head 72 and seat 52 and block fluid flow about pin 70 through bore 64.

In assembling catheter section 32 the end of tubing 12 extending from balloon 30B is force fitted into bore 51 of coupling part 50, and the end of tubing 12 extending through balloon 30A is similarly force fitted into bore 61 of coupling part 60, as shown in FIG. 5. The two coupling parts are then fitted together by inserting plug 65 into bore 55 with O-ring 68 tightly sealing against the wall of bore 55 to a point at which the left end of plug 65 almost abuts the bottom of bore 55 and stud 66 snaps into recess 56. In this position the facing ends of the two pins 70 strike each other and lift heads 72 off conical seats 52 and 62, respectively, opening fluid communication between bore 51 and bore 61 through bores 54 and 64 about pins 70, as shown in FIG. 5.

In FIGS. 6-9 a series of steps are illustrated showing the use of the invention in treating an aneurysm. In these drawings, the reference letter V generally designates a portion of the arterial system including an aneurysm A. In treating aneurysm A utilizing the device of this invention, reference is first made to FIG. 6.

An incision I is made in a part of system V through which communication can readily be made with the interior of aneurysm A. The closed end 16 of catheter 10 then is inserted into incision I and fed through arterial system V to a position at which the balloon forming structures 30A and 30B are on opposite sides of aneurysm A. It should be noted that the spacing of catheter section 32 is preset for example, by adjusting the length of tubing 12 passing through balloon forming structure 30A and leading to coupling member 60 such that the two balloon forming structures will be properly spaced to fit, and the precise location of catheter 10 in arterial system V can be established by feeling to determine its precise location.

Stopcock 22 is then positioned such that communication between bore 14 and the interior of barrel 28 is open. Plunger 26 is then introduced into barrel 28 to a position in which balloon forming structures 30A and 30B are inflated into contact with the walls of the blood vessels in system V on opposite sides of aneurysm A as shown in FIG. 7. Stopcock 22 is then moved to the closed position with blood flow on both sides of aneurysm A obturated. As shown in FIG. 7, an incision W is made in aneurysm A exposing catheter section 32 such that the surgeon can manipulate coupling members 50 and 60 to pull them apart without dislodging inflated balloons 30A and 30B. As coupling members 50 and 60 are pulled apart, compression springs 73 force valve pins 70 to move to a position as shown in FIGS. 3 and 4 holding annular gaskets 71 in compression between heads 72 and seats 52 and 62, respectively, thus, sealing the now separated catheter parts and retaining balloon forming structures 30A and 30B inflated.

Figure 8:
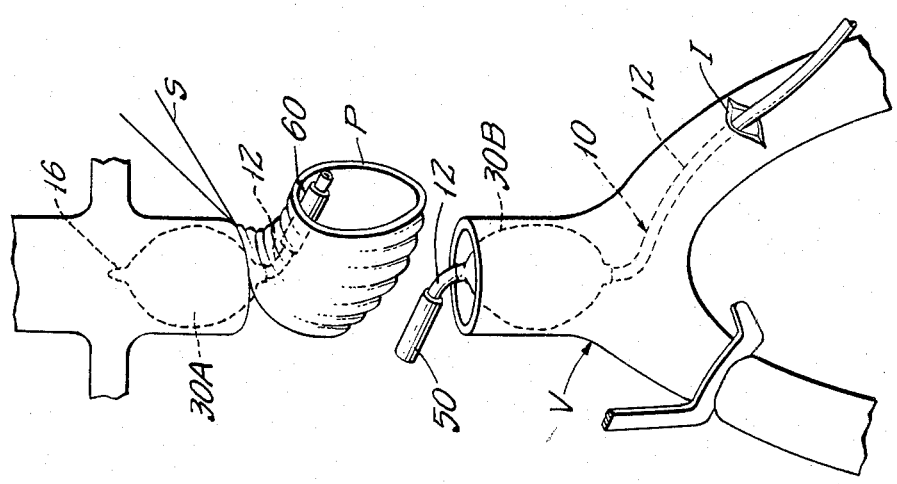

The section of arterial system V including aneurysm A is then resected to remove that portion of the blood vessel containing aneurysm A, and a prothesis P in the form of tubing of suitable inert material is then positioned over one of coupling members 50 and 60, as shown in FIG. 8, and held in place by making a tack with suture S to the adjacent resected end of the blood vessel.

Figure 9:
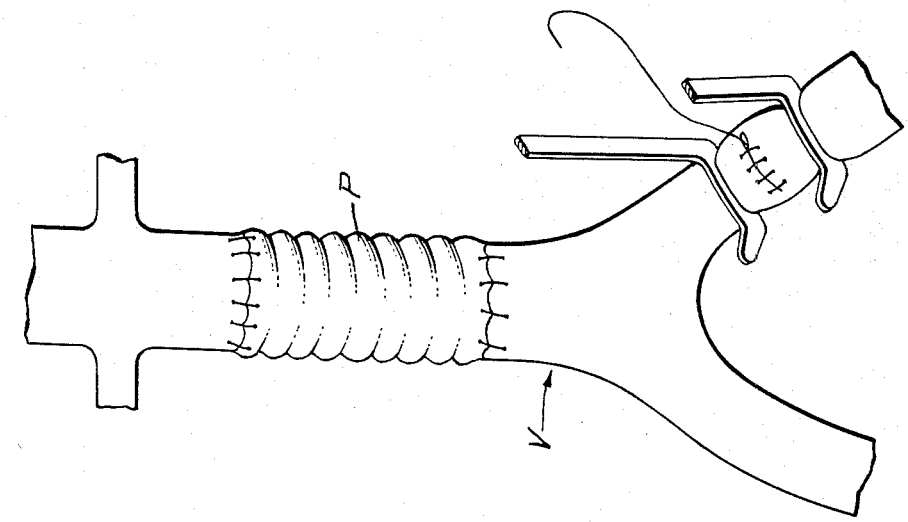

Coupling members 50 and 60 are then manipulated to bring them back together and insert plug 65 into bore 55 to the locking position with stud 66 in opening 56, re-establishing fluid communication through catheter section 32. Suturing prothesis P in place of the resected aneurysm is then completed. Stopcock 22 is then again moved to open position, and plunger 26 is withdrawn from barrel 29 deflating balloon forming structures 30A and 30B. Catheter 10 is withdrawn through incision I, which is then closed as shown in FIG. 9.

We claim:

1. A catheter which comprises an elongated tube having a central bore extending the length thereof, said bore being closed at one end of said catheter and having means for introducing a pressurized fluid into said bore at the other end of said catheter, said catheter further including first balloon forming structure including expandable wall means disposed about said tube located adjacent the closed end of said catheter, second balloon forming structure including expandable wall means disposed about said tube located along the length thereof spaced from said first balloon forming structure, said wall means being expandable to an inflated position responsive to pressurized fluid in said bore at the location of the associated balloon forming structure, and a separable coupling connected in said tube between said first and second balloon forming structures, said coupling including a first coupling member connected to said tube adjacent said first balloon forming structure and a second coupling member connected to said tube adjacent said second balloon forming structure, said coupling members having an engaged position and a separated position, and each said coupling member including valve means normally closed in said separated position of said coupling members and operable to open position in said engaged position of said coupling members whereby fluid communication in said bore between said balloon forming structures is open in said engaged position of said coupling members and is closed in said separated position of said coupling members.

2. A catheter according to claim 1 in which each said expandable wall means comprises a cylindrical wall enclosing said tube, and sealed at the ends thereof to said tube thereby trapping an annular closed space between said wall and said tube and port means in said tube communicating the interior bore thereof with said annular closed space.

3. A catheter according to claim 1 in which each said valve means includes a reciprocable pin, said pins being positioned to engage upon positioning said first and second coupling members in said engaged position of said coupling.

4. A catheter according to claim 2 in which each said valve means includes a reciprocable pin, said pins being positioned to engage upon positioning said first and second coupling members in said engaged position of said coupling.

* * * * *